US010926026B2

(12) United States Patent
Chassot et al.

(10) Patent No.: US 10,926,026 B2
(45) Date of Patent: Feb. 23, 2021

(54) INJECTION SYSTEM

(71) Applicant: ACIST MEDICAL SYSTEMS, INC., Eden Prairie, MN (US)

(72) Inventors: Pierre Yves Chassot, Thoiry (FR); Règis Chrétien, Neydens (FR)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 0 days.

(21) Appl. No.: 16/766,793

(22) PCT Filed: Nov. 26, 2018

(86) PCT No.: PCT/EP2018/082481
§ 371 (c)(1),
(2) Date: May 26, 2020

(87) PCT Pub. No.: WO2019/105872
PCT Pub. Date: Jun. 6, 2019

(65) Prior Publication Data
US 2020/0297922 A1 Sep. 24, 2020

(30) Foreign Application Priority Data
Nov. 28, 2017 (EP) .................................... 17204013

(51) Int. Cl.
*A61M 5/142* (2006.01)
*A61M 5/00* (2006.01)
(Continued)

(52) U.S. Cl.
CPC ........ *A61M 5/14232* (2013.01); *A61M 5/007* (2013.01); *F04B 43/1261* (2013.01);
(Continued)

(58) Field of Classification Search
CPC .............. A61M 5/14232; A61M 5/007; A61M 2205/505; A61M 2205/52; F04B 43/1261; A61B 6/032
(Continued)

(56) References Cited

U.S. PATENT DOCUMENTS 4,685,902 A 8/1987 Edwards et al.
4,735,558 A 4/1988 Kienholz et al.
(Continued)

FOREIGN PATENT DOCUMENTS

EP 0521184 A1 1/1993
EP 0523354 A1 1/1993
(Continued)

OTHER PUBLICATIONS

International Search Report and Written Opinion for PCT/EP2018/082481, dated Feb. 21, 2019.

*Primary Examiner* — Phillip A Gray
(74) *Attorney, Agent, or Firm* — Vivicar Law, PLLC

(57) ABSTRACT

A peristaltic pump (200) is proposed which comprises a first housing component (210) and a second loading component (230), said second loading component being at least partially contained within said first housing component and being axially movable with respect to said first housing component inside thereto. The second loading component further comprises at least a couple of rollers (235) which engage and squeeze a delivery tube (146) for delivering a fluid passing there through when, in operation, the second loading component is fully snapped into said first housing component. Moreover the second loading component comprises a guiding path (240) for guiding the delivery tube around said at least a couple of rollers towards an exit port (244) which is provided at a distal end surface of the second loading component. The present invention also relates to a patient set
(Continued)

and to an injection system comprising said peristaltic pump, as well as to a method of operating said injection system.

24 Claims, 7 Drawing Sheets

(51) Int. Cl.
*F04B 43/12* (2006.01)
*A61B 6/03* (2006.01)

(52) U.S. Cl.
CPC ........ *A61B 6/032* (2013.01); *A61M 2205/505* (2013.01); *A61M 2205/52* (2013.01)

(58) Field of Classification Search
USPC ........................................................ 604/508
See application file for complete search history.

(56) References Cited

U.S. PATENT DOCUMENTS

| | | | |
|---|---|---|---|
| 5,249,937 | A | 10/1993 | Aubert |
| 8,062,009 | B2 | 11/2011 | Cueni |
| 8,272,857 | B2 * | 9/2012 | Norman ................. F04B 43/08 |
| | | | 417/474 |
| 9,446,185 | B2 | 9/2016 | Yodfat et al. |

FOREIGN PATENT DOCUMENTS

| | | | |
|---|---|---|---|
| EP | 0932423 | B1 | 12/2003 |
| FR | 2753103 | B1 | 12/1998 |
| WO | 2017137421 | A1 | 8/2017 |

* cited by examiner

INJECTION SYSTEM

CROSS-REFERENCE TO RELATED APPLICATIONS

This application is the national stage application of corresponding international application number PCT/EP2018/082481, filed Nov. 26, 2018, which claims priority to and the benefit of European application no. 17204013.1, filed Nov. 28, 2017, all of which are hereby incorporated by reference in their entirety.

TECHNICAL FIELD

The present disclosure relates to the field of medical equipment. More specifically, the present disclosure relates to injection systems of medical fluids. Even more specifically, the present disclosure relates to injection systems comprising reusable peristaltic pumps.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

The injection of fluids into patients is commonplace in several medical procedures. For example, a contrast agent (or contrast medium) may be injected, possibly along with a saline solution, to enhance contrast of target (body) features (for example, human body's structures or organs) within the patients during scan examinations thereof. Particularly, in imaging applications (wherein a visual representation of the interior of the patients is created in a non-invasive way without turning to surgery techniques) the use of a contrast agent makes the target features more conspicuous. As a result, target features that would otherwise be less distinguishable from other nearby features (for example, surrounding tissues) are advantageously highlighted. This significantly facilitates the task of clinicians in diagnostic applications, and particularly in the identification and/or characterization of lesions, the monitoring of their evolution or the response to medical treatments. For example, a iodine-based contrast agent (such as comprising iopamidol) is commonly used in Computed Tomography (CT) applications (such as angiography investigations).

The contrast agent is usually injected into a blood vessel of a patient by an (automated) injection system. The injection system pressurizes the contrast agent and injects it into the patient's vasculature or organ under predetermined injection conditions, for example at a predetermined flow rate and volume. In this way, the contrast agent may be injected in a controlled, safe and efficient manner.

Therefore, an injection system is typically provided with one or more supply stations for supplying the contrast agent and/or the saline solution from a corresponding container (e.g. a bottle, a bag or a pouch). The injection system is further provided with a delivery arrangement that is in fluid communication with the at least one supply station. Since the delivery arrangement is positioned upstream of the pressurizing unit and, therefore, it is not in direct connection with a patient, with substantially no risk or a very low risk of cross-contamination, generally the delivery arrangement is a disposable element that is changed periodically (for example, every 10 or 12 hours). This means that the delivery arrangement is not changed when a new patient undergoes an examination and it is typically kept in place for multiple successive injections, till the predetermined period of time designed for the delivery arrangement is fully elapsed.

The automated injection systems known in the art and presently available on the market are divided into two main groups: syringe injectors (like Empower CTA or Empower CTA+ manufactured by Bracco Injeneering SA) and syringe-less injectors (like CT Exprès manufactured by Bracco Injeneering SA).

The present invention is directed to syringe-less injectors comprising a peristaltic pump that houses a plurality of rollers, among which a delivery tube is inserted, and sequentially and alternately squeezed for finally injecting a medical fluid (i.e. a contrast agent or two different contrast agents, a saline solution or a mixture thereof) into a patient.

More in detail, the present invention is directed to syringe-less injectors that comprise a peristaltic pump detachably engaged with the pressurizing unit of the injector, said peristaltic pump being discarded any time a new patient is admitted to an imaging room for a new examination to be performed (e.g. a CT scan examination).

The Applicant has perceived the need of providing a syringe-less injector with a reusable peristaltic pump so that at the end of each injection procedure only a very limited number of disposable components is required to be discarded, while other mechanical components, that do not run any major risk of pathogen contamination (and thus of cross-contamination among successive patients treated with the same injection system), are not requested to be thrown away and can be suitably and safely reused more times.

It is apparent that a reusable peristaltic pump represents a very attractive solution since it has a favorable impact on the healthcare system costs and it is more ecological due to the lower amount of parts to be discarded.

Some reusable technical solutions are already known in the medical field, especially with respect to medical infusion of a drug substance.

For instance, document U.S. Pat. No. 9,446,185 B2 discloses devices and methods for delivering a therapeutic fluid to a patient's body. The devices may comprise a dispensing unit having a reservoir, a driving mechanism having a movable member for delivering therapeutic fluid to a patient's body, at least one sensor for sensing a relative position of the movable member and generating a signal, and a processor for controlling the driving mechanism to deliver an amount of therapeutic fluid that compensates for a change in the flow of the therapeutic fluid occurring during fluid delivery. FIGS. 3 and 4 show an example of a two-part dispensing unit before and after the reusable part and the disposable part are connected. The reusable part includes a peristaltic pumping mechanism having a rotary wheel with four rollers, and the disposable part includes a delivery tube.

Document U.S. Pat. No. 4,685,902 discloses a disposable reservoir cassette for use with a roller pump delivery system, the disposable reservoir cassette comprising a flexible reservoir tube, an air-permeable, liquid-impermeable element engaging one end of the reservoir tube, a pierceable delivery septum engaging the other end of the reservoir tube and a rigid housing containing the reservoir tube. The housing includes a backstop which supports the tube in a circular path while allowing access to the septum. The housing is adapted to be secured to the roller pump such that the circular path of the tube is adjacent to the path of a pump roller wherein motion of the pump roller compresses the reservoir tube sufficiently to drive any fluid contained therein in the direction of the delivery septum.

Document FR 2,753,103 discloses a miniature peristaltic pump comprising a first and a second module each provided with means for coupling them: the first module, called pump module, comprising a rotor provided with three pressing rollers, means for driving said rotor and means for controlling said drive means; the second module, called cassette module, comprising a support piece with a rounded portion which, when the two modules are coupled, is substantially concentric to the rotor. The cassette module comprises means for receiving interchangeably a flexible pipe connected to—and forming an inseparable part of—a reservoir of medicinal solution and for its automatic positioning such that when the two modules are coupled, it is brought to bear against the rounded portion to be compressed by the rollers, the pipe and the reservoir thus forming a third module, called reservoir module, which can be easily replaced by another after use. This invention is useful for the subcutaneous or intravenous injection of medicinal solutions.

Document EP 521,184 discloses a portable pump for the administration of a therapeutic liquid, equipped with an integral reservoir. The object of the invention is to produce a pump in at least two modules, in which sterilisable and non-sterilisable elements are distributed, the operation of the pump being provided as soon as the various modules are assembled, and the separation of the modules bringing about the irreversible stopping of the pump. This object is achieved with the aid of a pump consisting of a reservoir module comprising a reservoir of medication and at least one duct linking the reservoir to the output of the pump and of a motor module comprising pumping means, drive means and control means. This pump is particularly intended for patients who have to receive medication continuously in small doses.

Document EP 523,354 discloses a medical peristaltic pump. The aim of the invention is to improve the pumping and leaktightness qualities of this pump, as well as to improve the flexibility of use of this pump whilst retaining a high safety level. This aim is achieved using a peristaltic pump in at least three modules, allowing a liquid substance to be administered and comprising pumping means housed in a first module and allowing compression of at least one pipe connecting a storage reservoir of the said liquid substance to the output of the pump, this compression being effected against at least one support component, forming a second module, these first and second modules being fitted with first positioning means and first assembly means so as to define a unit of two modules in which there is a squashing of the pipe which is necessary and sufficient to pump the said liquid substance and in that this unit of two modules and a third module are fitted with second positioning means and with second assembly means, so that once assembled together, the third module ensures the leaktightness of the pumping means.

It can be highlighted that the solutions disclosed by EP 521,184 and EP 523,354 concern peristaltic pump devices which are worn by a patient for guaranteeing a therapeutic liquid administration on a regular basis (e.g. hourly, daily, . . . dosage administrations). These devices are not reusable once the reservoir is emptied and thus they do not envisage any technical solution which allows the delivery tubes to be loaded into and unloaded from the peristaltic pump in order to be substituted with new ones. In fact, the delivery tubes are fixedly positioned in the reservoir module of the peristaltic pump where they are engaged and squeezed by the rollers so that the therapeutic liquid can be transferred from the reservoir to an exit port present on the reservoir module, said exit port being finally connected to a needle catheter for delivering the therapeutic liquid to a patient.

Document U.S. Pat. No. 8,062,009 (in the name of the same Applicant) discloses a peristaltic cassette casing comprising a tube housing forming an arc which comprises tube fixing means arranged along said housing so as to prevent the longitudinal displacement of a tube arranged in said housing.

Document WO 2017/137421 (in the name of the same Applicant) discloses a solution for operating an injection system comprising a pressurizing unit and at least one supply station for supplying a medical fluid to the pressurizing unit, the supply station comprising at least one receptacle for containing said medical fluid, a delivery arrangement in fluid communication with the receptacle and the pressurizing unit for delivering the medical fluid to a patient, and clamping means associated with the delivery arrangement for regulating the flow of the medical fluid through the delivery arrangement. The method comprises the steps of: operating the pressurizing unit till a first injection procedure is completed; maintaining the injection system in a standby condition before a second injection procedure is started, and operating the pressurizing unit till the second injection procedure is completed. The step of maintaining the injection system in a standby condition comprises the step of acting on the clamping means for de-clamping the delivery arrangement.

As already mentioned above, a removable and reusable peristaltic pump has some attractive advantages for the manufacturer of an injection system as well as for the user thereof, especially in terms of associated costs and lower environmental impact.

However the Applicant has noticed that a removable and reusable peristaltic pump has to face and solve some relevant technical issues which can negatively affect the safe and correct functioning of the injector system comprising said peristaltic pump.

In fact, if a reusable peristaltic pump is envisaged, this means that the majority of the pump components are suitable for a multi-patient use (i.e. they are not discarded after each treated patient), while the delivery tube, which is inserted into the pump and is compressed by the pump rollers for allowing advancement (and thus injection) of the medical fluid there through, is used for one single patient only and thus a new delivery tube has to be provided at the beginning of any new examination procedure.

However the step of loading the delivery tube within the peristaltic pump represents a critical aspect and thus it should be carried out with the greatest accuracy. In fact, it is necessary that sterility of the system is not compromised in order to avoid major contamination by pathogens that could be potentially introduced into the injection system due to excessive handling by the user of the many removable, reusable and/or disposable components of said injection system. This is clearly not a problem for the actual syringeless injectors (like CT Exprès manufactured by Bracco Injeneering SA) according to which the peristaltic pump and the delivery tube are a single disposable component (generally known in the field as Patient Set) which is provided to the user in a sterile (aseptic) package. In this case, in fact, the user introduces the peristaltic pump into a slot of the injector head and thus he is not requested to manually load and manipulate the delivery tube since the latter is already positioned inside the peristaltic pump during manufacturing and assembling of the Patient Set.

Moreover, if a user is requested to manually load the delivery tube into the peristaltic pump, he may run the risk of not performing this step properly, thereby kinking, pinching or in any case damaging the delivery tube, fact which can adversely affect the correct operation of the peristaltic pump and not guarantee the predetermined medical fluid injection parameters.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In looking for a reusable peristaltic pump which is suitable for overcoming the sterility and mechanical integrity issues mentioned above, the Applicant has perceived the need of performing a safe and guided loading of the delivery tube inside the peristaltic pump in order to substantially avoid any unnecessary manual handling of the delivery tube as well as any tricky and prolonged arrangement thereof for properly matching the tortuous path along the rollers periphery of the peristaltic pump.

The Applicant has found that this result can be achieved by designing the peristaltic pump to comprise two distinct parts which are coupled together through a relative axial sliding (snapping) movement that allows a guided and safe loading of the delivery tube inside the peristaltic pump.

Particularly, an aspect of the present disclosure provides for a peristaltic pump comprising a first housing component and a second loading component, said second loading component being at least partially contained within said first housing component and being axially movable with respect to said first housing component inside thereto, said second loading component comprising at least a couple of rollers for engaging and squeezing a delivery tube when, in operation, the second loading component is fully snapped into said first housing component, the second loading component further comprising a guiding path for guiding the delivery tube around said at least a couple of rollers towards an exit port provided at a distal end surface of the second loading component.

Furthermore, the present disclosure relates to a patient set comprising a peristaltic pump and a delivery tube received within said peristaltic pump, the latter comprising a first housing component and a second loading component, said second loading component being at least partially contained within said first housing component and being axially movable with respect to said first housing component inside thereto, said second loading component comprising at least a couple of rollers for engaging and squeezing the delivery tube when, in operation, the second loading component is fully snapped into said first housing component, the second loading component further comprising a guiding path for guiding the delivery tube around said at least a couple of rollers towards an exit port provided at a distal end surface of the second loading component.

Moreover, the present disclosure also relates to an injection system comprising a reusable and at least partially removable peristaltic pump which includes a housing component and a loading component, the loading component being axially movable within the housing component, and the rollers possessed by the loading component engaging a delivery tube when the loading component is fully snapped into the housing component.

In detail, an aspect of the present disclosure provides for an injection system comprising:
  at least one supply station for supplying a medical fluid to be injected into a patient's vasculature;
  a pressurizing unit comprising a motor for pressurizing the medical fluid received from said at least one supply station;
  a delivery arrangement in fluid communication with said at least one supply station, and
  a patient set in fluid communication with said delivery arrangement for delivering the pressurized medical fluid to the patient, said patient set including a peristaltic pump which comprises a first housing component and a second loading component, said second loading component being at least partially contained within said first housing component and being axially movable with respect to said first housing component inside thereto, said second loading component comprising at least a couple of rollers for engaging and squeezing a delivery tube when, in operation, the second loading component is fully snapped into said first housing component, the second loading component further comprising a guiding path for guiding the delivery tube around said at least a couple of rollers towards an exit port provided at a distal end surface of the second loading component.

Furthermore, the present disclosure also relates to a method of operating an injection system comprising said reusable peristaltic pump.

In detail, a further aspect of the present disclosure provides for a method of operating an injection system comprising: a pressurizing unit, at least one supply station for supplying a fluid to the pressurizing unit and a peristaltic pump coupled with said pressurizing unit, said peristaltic pump comprising a first housing component and a second loading component, said second loading component comprising at least a couple of rollers and a guiding path, said method comprising the steps of:
  axially retracting in a distal direction the second loading component with respect to the first housing component, so that the peristaltic pump (200) reaches an opened loading configuration;
  positioning a delivery tube about said at least a couple of rollers and along said guiding path towards an exit port of the second loading component;
  snapping said second loading component into said first housing component so that the peristaltic pump (200) reaches a closed operative configuration, and
  operating the pressurizing unit to rotate the at least a couple of rollers for engaging and squeezing the delivery tube.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
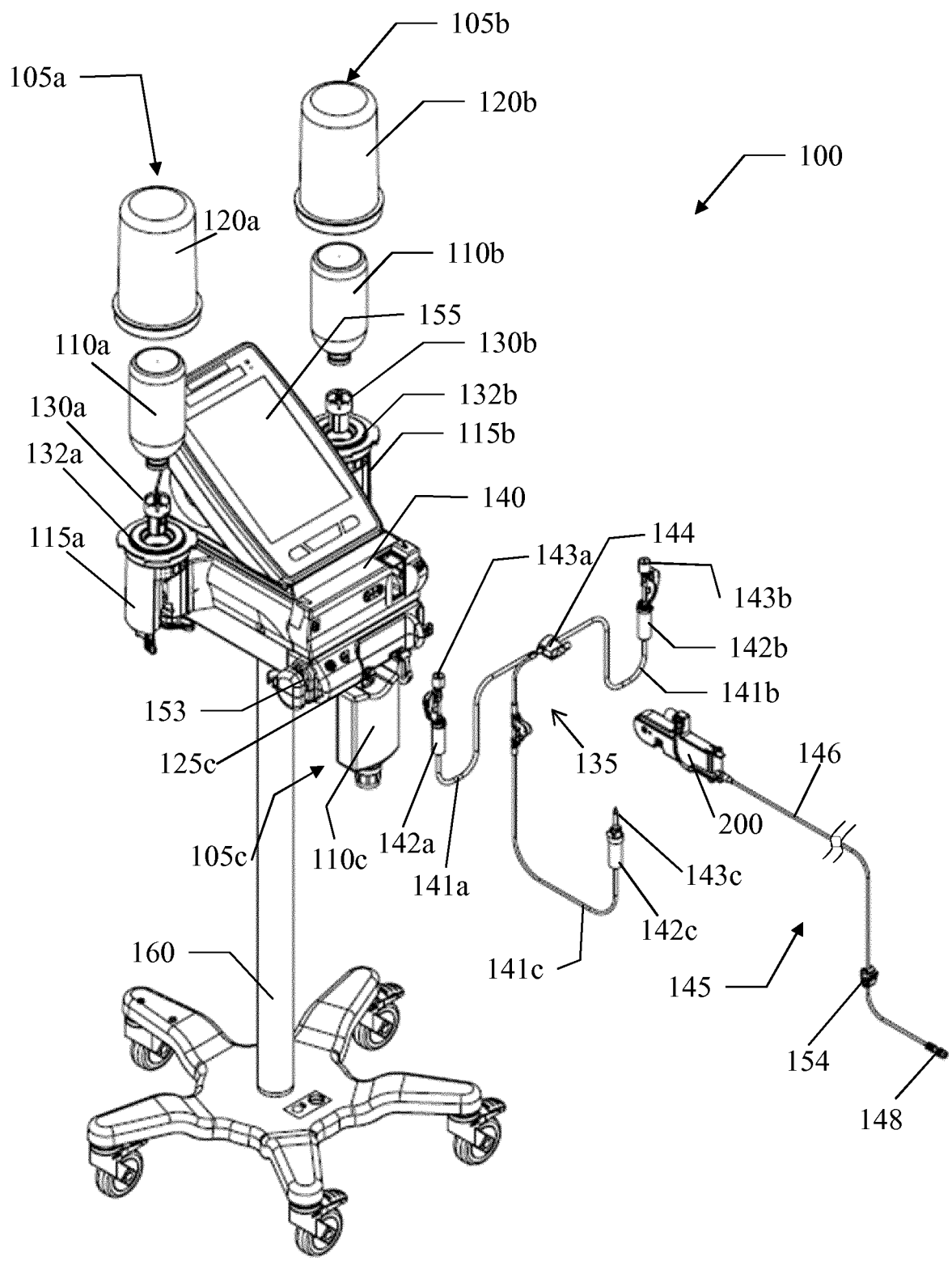
FIG. 1 shows a pictorial representation in partially exploded perspective view of an injection system wherein the solution according to an embodiment of the present disclosure may be applied.

With reference in particular to FIG. 1, a pictorial representation in partially exploded perspective view is shown of an injection system 100 wherein the solution according to an embodiment of the present disclosure may be applied.

The injection system 100 is used to inject one or more medical fluids into a patient (not shown in the figure). Particularly, the injection system 100 is an automated syringe-less injector that is used by clinicians to inject contrast agent and saline solution during scan examinations (for example, in radiography applications like CT scans).

The injection system 100 shown in FIG. 1 comprises a first supply station 105a, a second supply station 105b and a third supply station 105c for supplying the medical fluids to be injected from corresponding receptacles. Particularly, the supply station 105a and the supply station 105b supply a medical fluid from a bottle 110a and from a bottle 110b, respectively (i.e., a container made from glass or rigid plastic). On the contrary, the supply station 105c supplies a medical fluid from a pouch 110c (i.e., a container made from soft plastic). The supply stations 105a, 105b may be used to supply one or more contrast agents (to enhance contrast of specific body features within the patient), or a contrast agent and a saline solution (comprising a physiological or isotonic solution) respectively, whereas the supply station 105c may typically be used to supply the saline solution. For example, in CT applications the contrast agent may be a iodine-based contrast agent comprising diatrizoate, ioxaglate, iopamidol, iohexol, ioxilan, iopromide or iodixanol, and the saline solution may be sodium chloride. An example of a commercial contrast agent comprising iopamidol is ISOVUE, manufactured by Bracco Diagnostics Inc. (trademarks). Each bottle 110a, 110b may contain a single or multiple dose (for example, 50-500 ml) of different contrast agents (a first contrast agent in the first bottle and a second different contrast agent in the second bottle, the two contrast agents to be supplied according to a predetermined sequence) or of the same contrast agent (to be supplied in succession to increase the duration of the scan examination). The pouch 110c generally contains a bulk of saline (for example, 100-1,000 ml) to be supplied before (pre-flush), after (post-flush) or between (interphase) injections of the contrast agent, or alternatively in rapid alternate succession with the contrast agent (to achieve a mixing of the contrast agent and the saline solution within an organ of the patient, for example within the heart). Alternatively, as mentioned above, the supply stations 105a and 105b may be used to supply a contrast agent and a saline solution, respectively. In this latter case the supply station 105c can be eliminated.

More specifically, each supply station 105a, 105b (respectively) comprises a bottle holder 115a, 115b for housing and supporting the bottle 110a, 110b. A protective cover 120a, 120b may be mounted on the bottle holder 115a, 115b to cover the bottle 110a, 110b when it is held thereon, thereby defining a (closed) chamber for housing the bottle 110a, 110b. The bottle holder 115a, 115b and the protective cover 120a, 120b protect the bottle 110a, 110b from external accidental shocks. Moreover, typically the protective cover 120a, 120b are made of a thermally insulating material (for example, polycarbonate) to reduce heat losses, thereby helping to maintain warm (for example, at about the body temperature) the medical fluid contained in the bottle 110a, 110b, which was previously heated in a dedicated device (not shown) separate from the injection system. Typically the supply station 105c simply comprises a hook 125c for hanging the pouch 110c.

The injection system further comprises a delivery arrangement 135 which determines a fluid pathway for conveying the medical fluids from the receptacles 110a, 110b, 110c to a pressurizing unit 140. The tubing of the delivery arrangement is made from a plastic material. Preferably the tubing of the delivery arrangement is made from PVC.

For this purpose, in each supply station 105a, 105b a bottle connector 130a, 130b is arranged in a connection port 132a, 132b of the bottle holder 115a, 115b. The bottle connector 130a, 130b comprises a spike for connecting to the bottle 110a, 110b and a connection element (for example, a septum or a male luer lock fitting) in fluid communication with the spike. The spike and the connection element are located at opposite longitudinal ends of the bottle connector 130a, 130b. Typically, the bottle connector 130a, 130b also comprises a filtering unit (not shown in the figure) between its spike and connection element. The bottle connector 130a, 130b is a disposable element for use with a single bottle 110a, 110b (for example, with the spike that breaks off and remains inside the bottle 110a, 110b when the bottle connector 130a, 130b is removed in order to prevent any accidental re-use thereof).

The delivery arrangement 135 (which is often indicated by the technicians as "Day Set" or "Transfer Set") connects all the supply stations 105a, 105b, 105c to the pressurizing unit 140 for transferring the corresponding medical fluids from the receptacles 110a, 110b, 110c to the pressurizing unit 140. The delivery arrangement 135 comprises a transfer line for each supply station 105a, 105b, 105c. The transfer line of each supply station 105a, 105b comprises a flexible tubing 141a, 141b that is provided (at a distal end thereof with respect to the pressurizing unit 140) with a reservoir (or drip chamber) 142a, 142b and a connection element 143a, 143b for mating with the connection element of the bottle connector 130a, 130b. For example, the connection element 143a, 143b is a spike in case the connection element of the bottle connector 130a, 130b is a septum, or the connection element 143a, 143b is a female luer lock fitting in case the connection element of the bottle connector 130a, 130b is a male luer lock fitting. During operation of the injection system 100, the reservoir 142a, 142b and the connection element 143a, 143b are arranged inside the bottle holder 115a, 115b. Analogously, the transfer line of the supply station 105c comprises a flexible tubing 141c that is provided (at a distal end thereof with respect to the pressurizing unit 140) with a reservoir (or drip chamber) 142c and a spike 143c for connecting to the pouch 110c. All the flexible tubings 141a, 141b, 141c are coupled (at their proximal ends with respect to the pressurizing unit 140) with a T-connector 144, which comprises a plug for insertion into a corresponding port of the pressurizing unit 140.

The injection system 100 further comprises a patient set 145 that connects the pressurizing unit 140 to the patient for delivering the pressurized medical fluids thereto. The patient set 145 comprises a delivery line made of a flexible tube 146, which is provided (at a distal end thereof with respect to the patient) with a peristaltic pump 200. The latter is introduced into a dedicated port provided in the pressurizing unit 140 and it is also put in fluid communication with the T-connector 144. The peristaltic pump 200 houses a rotor having a plurality of rollers (squeezing wheels), among which a corresponding portion of the flexible tube 146 is inserted.

The pressurizing unit 140 comprises an electric motor (not visible in the figures) which rotates the rotor (and thus also the corresponding rollers) of the peristaltic pump so that the latter pressurizes the medical fluids (received from the receptacles 110a, 110b, 110c via the delivery arrangement 135) for their injection into the patient (for example, up to a pressure of 17 bar, or at a flow rate from 0.5 to 9.9 ml/s).

When the patient set 145 is of single use type (as shown in FIG. 1) for use by a single patient only, the flexible tube is quite long and it is provided (at a proximal end thereof with respect to the patient) with a connection element 148 for mating with a respective corresponding connection element (for example, a plug) of a peripheral catheter (not shown) which is inserted through the skin into a peripheral vein of the patient to be treated. The flexible tube 146 can be also provided with a clip 154 that pinches the tube and closes the line during installation or uninstallation of the peripheral catheter.

Figure 2:
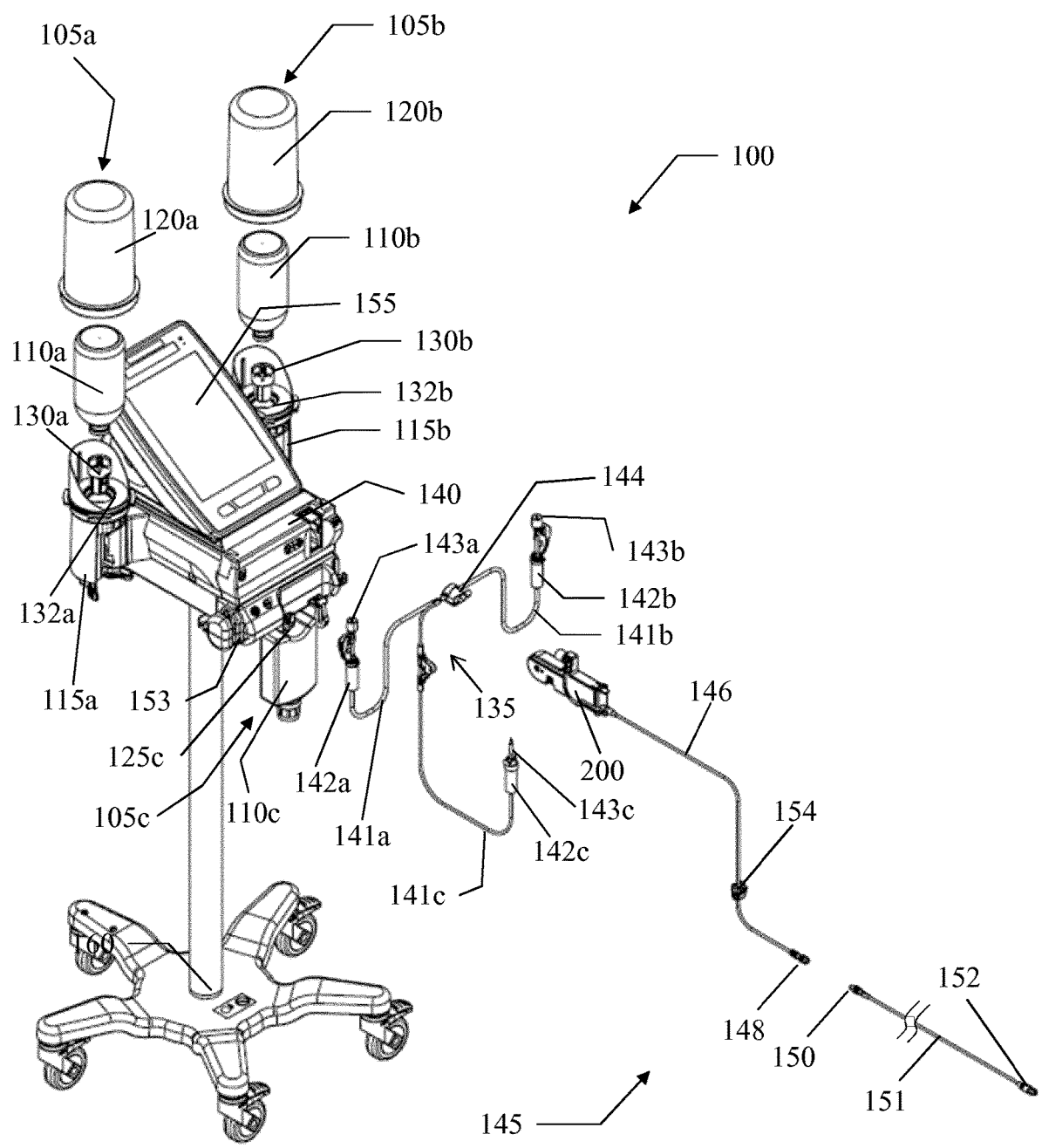
FIG. 2 shows a pictorial representation in partially exploded perspective view of an alternative injection system wherein the solution according to an embodiment of the present disclosure may be applied.

When the patient set 145 is of multiple use type (as shown in FIG. 2) for use with multiple patients, typically the flexible tube 146 (delivery line) is quite short and it is provided at the proximal end thereof with a connection element 148 for mating with a corresponding connection element 150 of an additional patient line (also indicated as patient line) 151 which is made of a quite long flexible tube. The additional patient line 151 ends with a connection element 152 for mating with a corresponding connection element possessed by a peripheral catheter (not shown). The flexible tube 146 can be also provided with a clip 154 that pinches the tube and closes the line during installation or uninstallation of the additional patient line 151.

The patient set 145 is a disposable element which, in case of single use (see FIG. 1), is for use entirely with a single patient, while, in case of multiple use (see FIG. 2), it is changed periodically (for example, every 12 hours), except for the additional patient line 151 which is for use with a single patient only and thus it is discarded at the end of each injection procedure for a given patient and it is substituted with a new one when a new patient is to be treated.

According to the embodiment shown in FIG. 1, each supply station 105a, 105b, 105c of the injection system 100 further comprises clamping means (not shown in the figures) for engaging the delivery arrangement 135, and thus blocking or unblocking the passage of the medical fluids flowing there into. Specifically, the clamping means of supply station 105a, 105b is located inside the bottle holder 115a, 115b, while the clamping means of supply station 105c is located in a dedicated seat 153 housed in the front part of the injector body. Activation (i.e. clamping and de-clamping) of the clamping means is controlled automatically by the injector software, i.e. it is part of the injection steps that are carried out by the injector (according to the injection protocols that are loaded on the injector, typically on the injector remote console not shown in the figures).

A control unit 155 controls the operation of the injection system 100. For example, the control unit 155 comprises a (main PCB) board with a microprocessor, a RAM that is used as a working memory by the microprocessor and a flash $E^2PROM$ that stores information to be preserved even when a power supply is off (particularly, a control program of the injection system 100). Moreover, the control unit 155 comprises a touch-screen and several buttons, which are used by an operator to interact with the control unit 155.

Most commonly the injection system 100 is supported by a stand 160. The stand 160 is provided with wheels to facilitate moving the injection system 100; moreover, the wheels have a foot brake to secure the injection system 100 in position. According to an alternative embodiment (not shown), the injection system is provided with a ceiling mount which allows installation of the injection system in the ceiling of the intervention/scan room.

Figure 3:
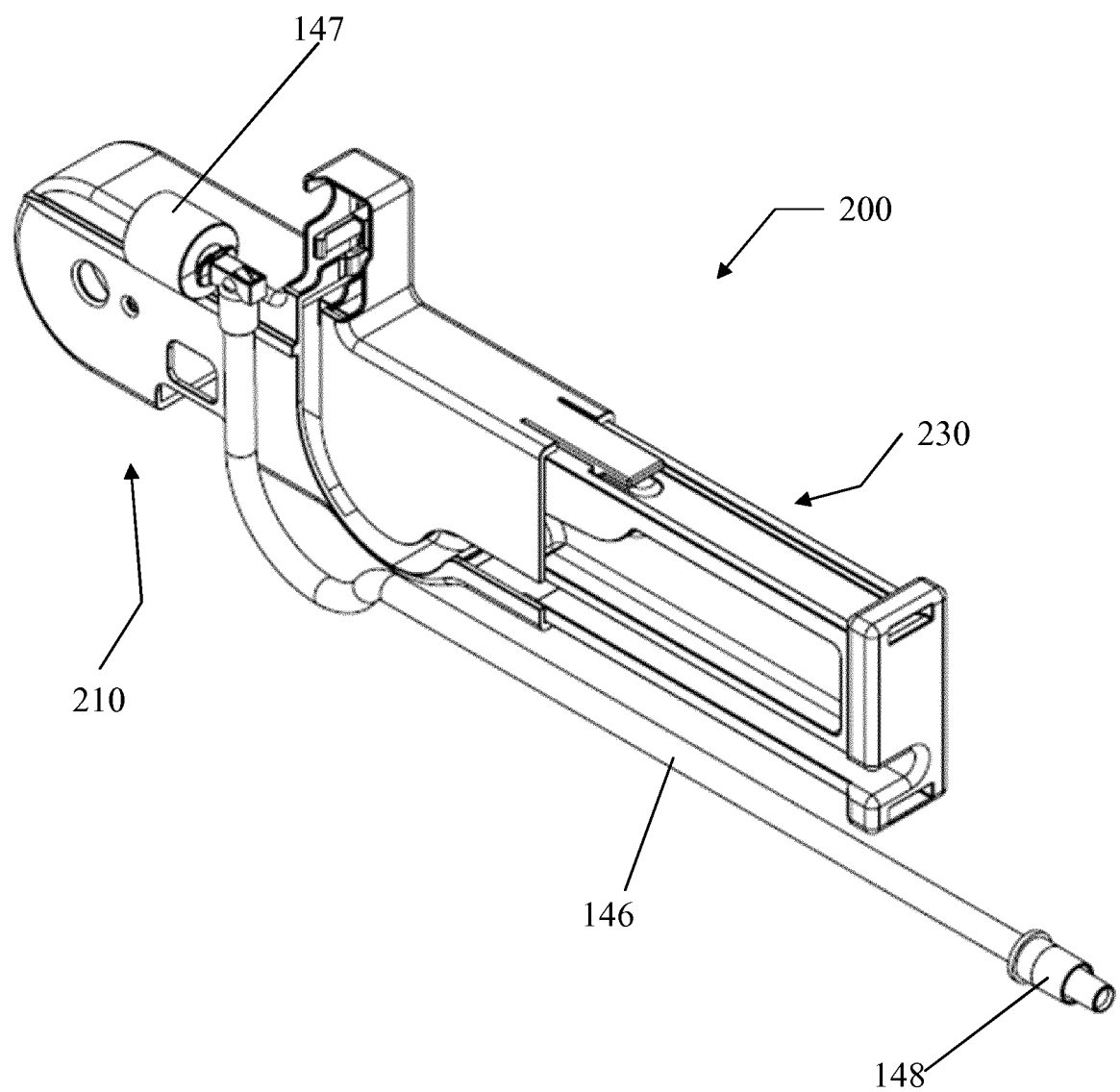
FIG. 3 shows a pictorial perspective view of a peristaltic pump according to an embodiment of the present disclosure, the peristaltic pump being ready to receive a delivery line before being inserted into a pressurizing unit of an injection system.

FIG. 3 shows a perspective view of a peristaltic pump 200 according to an embodiment of the present disclosure, wherein the peristaltic pump is ready to receive the delivery line 146 before being inserted into the pressurizing unit 140 of the injection system 100. The peristaltic pump 200 comprises two main components 210, 230 which slidably engage the one into the other along the longitudinal axes thereof and which define the peristaltic pump body and encumbrance.

Figure 4:
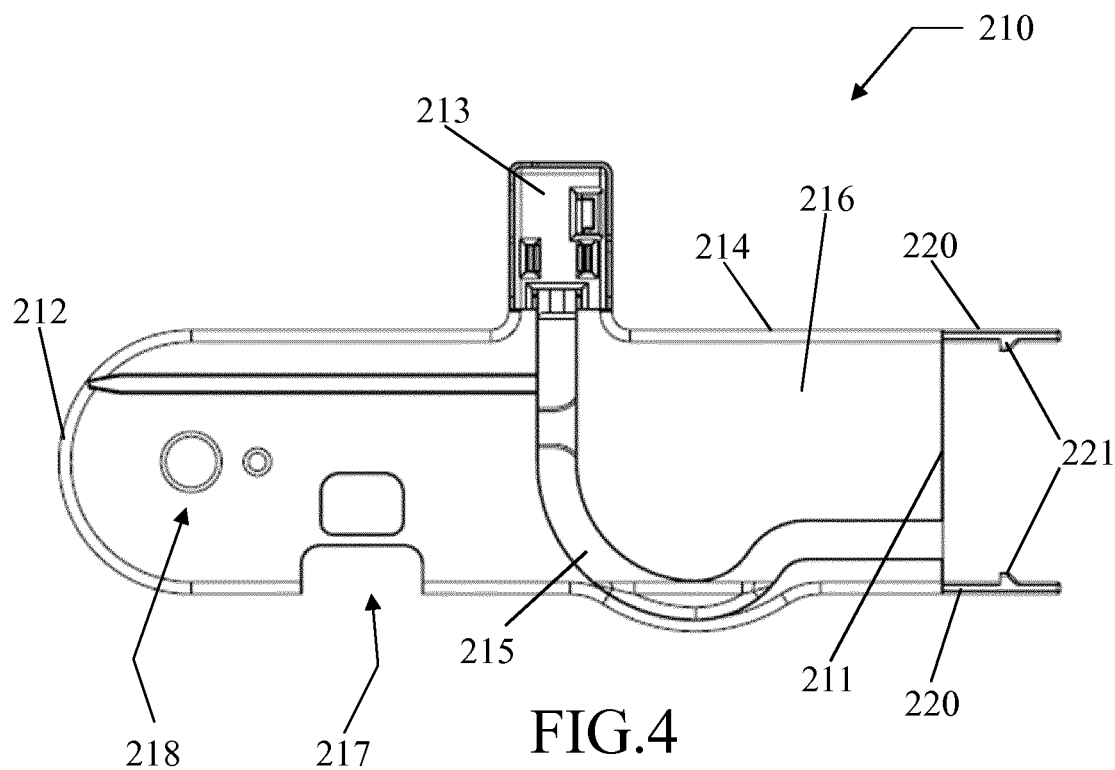
FIG. 4 and FIG. 5 show a lateral view and a perspective view, respectively, of a first housing component of the peristaltic pump according to the present disclosure.
Figure 5:
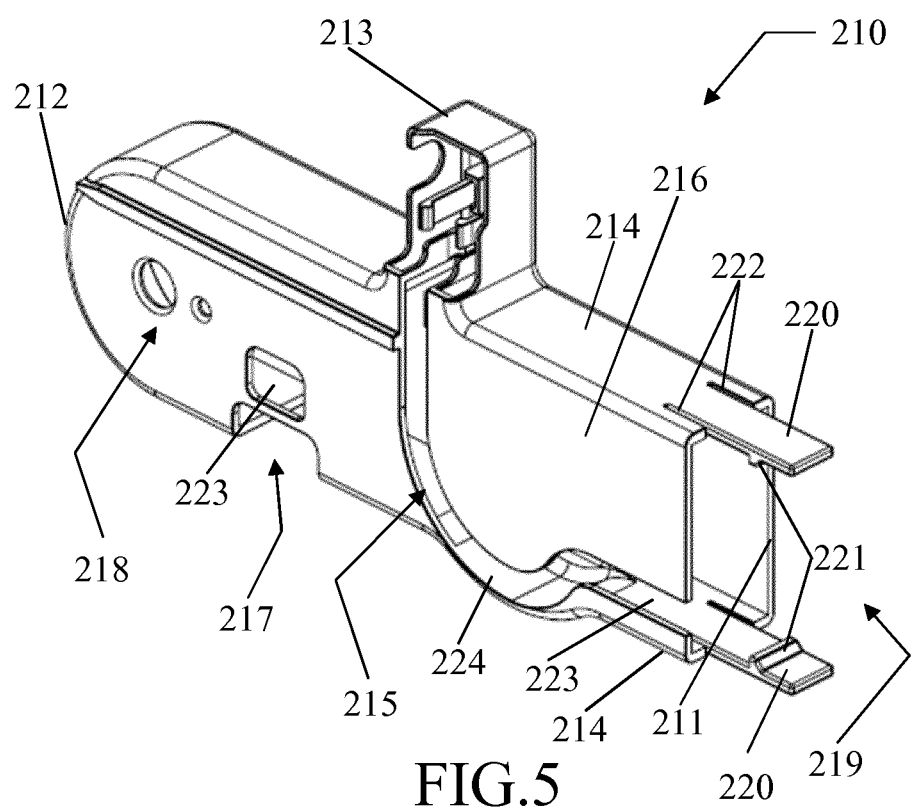

In detail, as better shown in FIG. 4 and FIG. 5, the first housing component 210 of peristaltic pump 200 constitutes and defines the pump external casing and it has a substantially parallelepiped shape which is opened at one of its axial ends for allowing the introduction of the second loading component 230 into the first housing component 210 through an axial sliding movement of the second loading component 230 with respect to the first housing component 210. Therefore, as clearly apparent from the lateral view shown in FIG. 4, the first housing component 210 has a substantially U-shape in longitudinal cross-section where its first (distal) end 211 is opened and its second (proximal) end 212 is closed. As mentioned above, the first (distal) end 211 is opened for allowing the second loading component 230 to be inserted into the first housing component 210, while the second (proximal) end 212 is closed for engaging the pump 200 inside a dedicated slot of the pressurizing unit 140.

The first housing component 210 further comprises a supporting element 213 for receiving the connection element 147 of the delivery tube 146, said connection element 147 being provided for mating with a corresponding connection element possessed by the T-connector 144 of the delivery arrangement (Day Set) 135, thereby putting the latter in fluid communication with the patient set 145. The supporting element 213 protrudes from a minor lateral surface 214 of the first housing component 210, in a direction substantially perpendicular to said lateral surface 214.

Moreover, the first housing component 210 comprises a guiding element 215 for allowing the user to properly install the delivery tube 146 within the peristaltic pump 200, as better described in the following of the present description. The guiding element 215 defines a path which is created in a major lateral surface 216 of the first housing component 210 and which connects the supporting element 213 with the opened first distal end 211 of the first housing component 210.

The first housing component 210 further comprises some specific geometry, generically indicated with reference 217 in FIG. 4 and FIG. 5, which includes suitable cuts and profiles for allowing the correct positioning and engagement of the peristaltic pump 200 within the injector head, specifically in correspondence of the pressurizing unit 140 of the injection system 100 and of the inserted air-pressure sensor. The first housing component 210 also comprises further specific geometries, generically indicated with reference 218 in FIG. 4 and FIG. 5, which include a suitable engaging area for coupling the peristaltic pump 200 to the motor axis thereof, said motor (not shown in the figures) being housed within the injector head and dragging to rotation the rollers 225 of the second loading component 230 (shown in FIG. 6 and FIG. 7). Said specific geometries also include an engaging area for laser detection that detects which kind of patient set is installed (e.g. if it is for single patient use or for multi-patient use) and verifies the correct functioning of the pump (e.g. that the motor speed is equal to the rollers speed, which means that relevant slipping phenomena are not detected).

The first housing component 210 also comprises blocking means 219 for reliably engaging and securing the first housing component 210 to the second loading component 230 when either the latter is fully inserted into the first housing component 210 and the peristaltic pump 200, with the delivery tube 146 engaged by the rollers 235 and the peristaltic pump, in its closed and operative configuration, is ready to be introduced into the pressurizing unit 140, or the second loading component 230 is engaged with the first housing component 210 in the peristaltic pump 200 opened configuration ready to receive a new delivery tube 146 or to discard a fully used delivery tube 146. In detail, the blocking means 219 includes a tab 220 and a small bump 221, the functioning thereof being explained in the following of the present description. The tab 220 extends from the axial opened end of said lateral surface 214 of the first housing component 210 in a direction substantially parallel to said lateral surface. In order to increase the flexibility of the tab 220, its longitudinal edges extend along a proximal direction (i.e. in a direction opposite to their longitudinal extension which protrudes from the opened first distal end 211 of the first housing component 210) by means of suitable cuts 222. The small bump 221 is provided at about the distal proximity of the tab 220, in correspondence of said first distal end 211, and it extends in a direction substantially perpendicular to said tab 220 and towards the interior of the first housing component 210. Preferably, the blocking means 219 is provided on both minor lateral surfaces 214 of the first housing component 210 so that a first blocking means 219 is arranged at the distal edge of the upper minor lateral surface 214 (i.e. the minor lateral surface which the supporting element 213 protrudes from) of the first housing component 210 and a second blocking means 219 is arranged at the distal edge of the lower minor lateral surface 214.

The internal part of the lower minor lateral surface 214 of the first housing component 210 (said internal part facing the interior hollow space of the first housing component 210 which is suitable for receiving the second loading component 230) comprises a substantially flat supporting area 223 on which a corresponding lower minor lateral surface of the second loading component 230 can slide when the latter engages, and is loaded into, the first housing component 210. The internal part of the lower minor lateral surface 214 of the first housing component 210 further comprises a curved depressed portion 224 which provides for a suitable loading space that guarantees a proper and correct positioning of the delivery tube 146 when the second loading component 230 has engaged the first housing component 210 and the peristaltic pump 200 is in its opened (loading) configuration.

On its opposite major lateral surfaces the first housing component 210 generally includes also a respective snapping area (not shown in the figures) that is pressed by the user for unlocking the peristaltic pump from the injector head.

Figure 6:
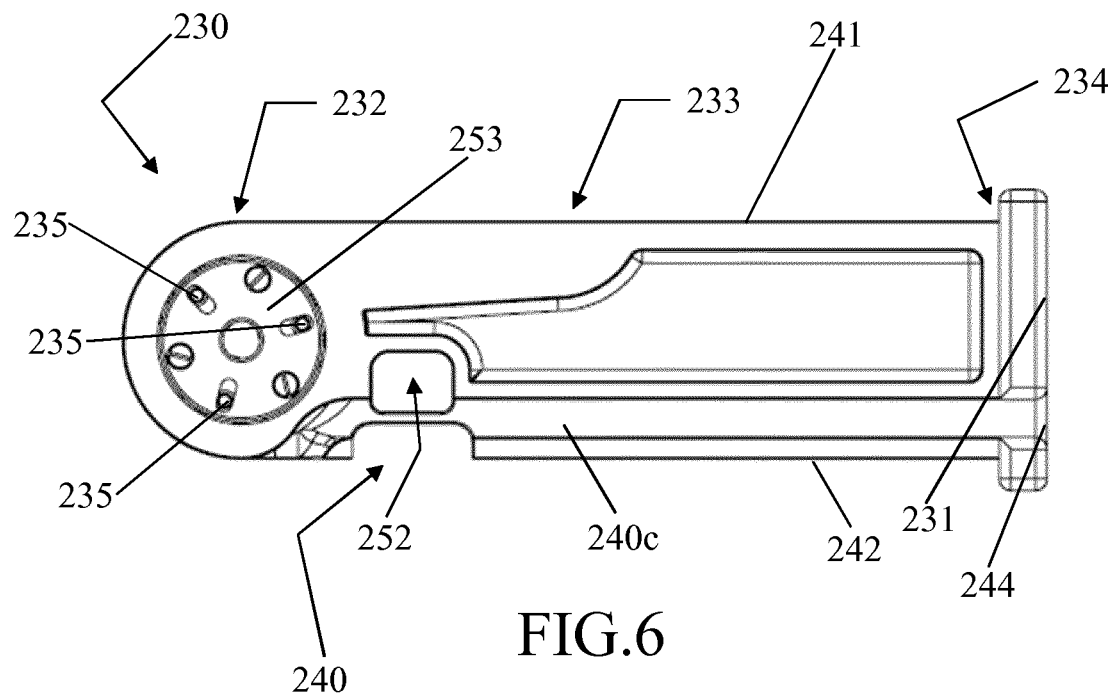
FIG. 6 and FIG. 7 show a lateral view and a perspective view, respectively, of a second loading component of the peristaltic pump according to the present disclosure.
Figure 7:
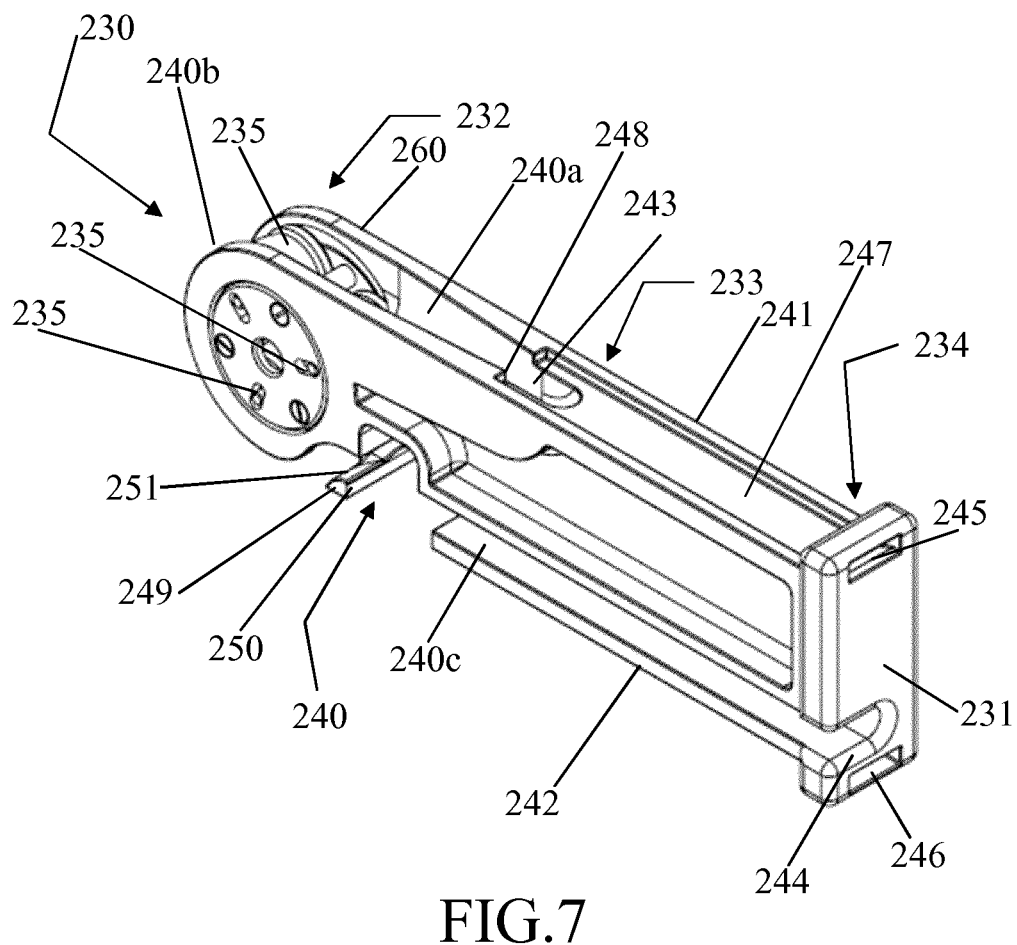

As better shown in FIG. 6 and FIG. 7, the second loading component 230 (also indicated as "loader" in the present description) has an external shape substantially matching the internal shape of the first housing component 210 so that, when the second loading component 230 is fully axially inserted into the first housing component 210, the two components have substantially the same length (longitudinal extension), except for the tabs 220 of the blocking means 219 which longitudinally protrude from the distal end surface 231 of the second loading component 230. In detail, the second loading component 230 comprises a first (proximal) end region 232, a central region 233 and a second (distal) end region 234. The first (proximal) end region 232 has a substantially circular shape (in longitudinal cross-section) which is suitable for housing the rollers 235 of the peristaltic pump 200. The embodiment represented in the figures includes three rollers, but a different number of rollers can be envisaged as well (e.g. from a minimum of two rollers to a maximum of four to six rollers).

The second loading component 230 comprises a guiding path 240 for receiving the delivery tube 146 which is squeezed by the rollers 235 when the first housing component 210 and the second loading component 230 are suitably engaged, the peristaltic pump 200 is introduced into the injection system 100 and the latter is activated (armed) to inject. The guiding path 240 extends along part of the upper minor lateral surface 241 of the second loading component 230 and along the lower minor lateral surface 242 of the second loading component 230. In detail, the guiding path 240 includes a first path 240*a* which is provided along the top portion of the second loading component 230 and which extends from the first (proximal) end region 232 to the central region 233 where it merges with the exit port 243 that, when the second loading component 230 is fully snapped into the first housing component 210, is located in correspondence of the supporting element 213 so that the delivery tube 146 can be guided into, and fixed to, said supporting element 213. The guiding path 240 also includes a second path 240*b* which surrounds the rollers and substantially extends around the circular profile of the first (proximal) end region 232. The guiding path 240 finally comprises a third path 240*c* which is provided along the bottom portion of the second loading component 230 and which extends from the first (proximal) end region 232 to the second (distal) end region 234 passing through the central region 233, so that the third path 240c finally merges to the exit port 244 at the distal end surface 231 of the second loading component 230. The guiding path 240 of the second loading component 230 cooperates with the guiding element 215 of the first housing component 210 to ensure a correct, safe and controlled positioning of the delivery tube 146 within the peristaltic pump 200.

The distal end surface 231 further comprises two small slots 245, 246 which are provided for receiving the corresponding tabs 220 of the blocking means 219 possessed by the first housing component 210. In fact, in order to properly ensure a safe and reliable engagement of the second loading component (loader) 230 within the first housing component 210, the tabs 220 are inserted into the corresponding slots 245, 246 till the small bumps 221 protrude outside the slots and abut against the distal end surface 231, thereby guaranteeing that the first 210 and the second 230 components are correctly engaged and the peristaltic pump is in its closed and loaded configuration. Disengagement of first 210 and second 230 components (for discarding the used delivery tube 146 and loading a new one) can be easily performed, for instance, by pushing radially outwardly on the corresponding tabs 220 and simultaneously axially translating (shifting) the first housing component 210 with respect to the second loading component 230 so that the bumps 221 can fully pass through the slots 245, 246.

During the loading operation of the delivery tube 146 into the peristaltic pump 200, in order to ensure that the second loading component 230 does not slide away and disengages from the first housing component 210, the upper minor lateral surface 241 and the lower minor lateral surface 242 of the second loading component 230 are each provided with a corresponding groove whose proximal edge is engaged by the corresponding small bump 221. FIG. 7 clearly shows the groove 247 possessed by the upper minor lateral surface 241 as well as the proximal edge 248 thereof that is engaged by the small bump 221 of the tab 220 protruding from the upper minor lateral surface 214 of the first housing component 210. The figures do not show the corresponding groove and proximal edge possessed by the lower minor lateral surface 242 of the second loading component 230.

Furthermore, the second loading component 230 comprises a ramp support 249 which protrudes from the back major lateral surface 260 of the second loading component 230 and which is positioned at the same planar level of the third path 240c, thereby forming part of the guiding path 240. The ramp support 249 has a lateral (vertical) side 250 which cooperates with the specific geometry 217 of the first housing component 210 in order to allow a proper placement of the air-pressure sensor (not shown) of the injector head. Moreover, the ramp support 249 has a smoothly inclined surface 251 which, in combination with the curved depressed portion 224 of the first housing component 210, facilitates the correct positioning and guiding of the delivery tube 146 from the second path 240b to the third path 240c of the guiding path 240.

Analogously to the first housing component 210, the second loading component 230 comprises some specific geometries, generically indicated with reference 252 and 253 in FIG. 6, which correspond to the specific geometries 217, 218 of the first housing component 210, so as to define suitable cuts, profiles and engaging areas for allowing the correct positioning and engagement of the peristaltic pump 200 in the injector head as well as the coupling of the peristaltic pump 200 to the motor axis thereof.

Preferably the peristaltic pump is made from a rigid plastic material (e.g. polycarbonate), a metallic material (e.g. aluminum) or a composite material (e.g. a fiber-reinforced polymer).

In operation, for each injection to be performed, the operator positions the injection system 100 close to the patient to be examined and then turns the injection system on. If not already done, the operator installs the delivery arrangement 135 by inserting each drip chamber 142a, 142b and each connection element 143a, 143b into the corresponding bottle holder 115a, 115b, thereby releasably blocking them therein (for example, by means of a snap-fit mechanism). When the pouch 110c (containing the saline solution) is not installed, the control unit 155 displays a message on its screen prompting the operator to do so. If the pouch 110c is to be used, the operator pierces a seal of the pouch 110c with the spike 143c, hangs the pouch 110c from the hook 125c and fills the reservoir 142c completely with the saline solution (by repeatedly squeezing it). At this point, the operator programs the control unit 155 (either at the control unit 155 or at an injector remote console not shown in the figures) by entering specific information relating to the saline solution of the pouch 110c (for example, its brand name and volume). Otherwise, if the pouch 110c is not used, the operator enters a corresponding command to the control unit 155 (or the remote console). In both cases, when the bottle 110a (with the contrast agent) is not installed, the control unit 155 displays a message on its screen prompting the operator to do so. In response thereto, the operator takes the bottle 110a from a separate warmer (not shown in the figures), wherein the bottle 110a has been pre-warmed to a target temperature. The target temperature is typically set to a value high enough to allow injecting the contrast agent efficiently (for example, at the desired flow rate) and comfortably for the patient, but not too high to be harmful for the patient. Typically the target temperature is in a range from 32° C. to 37.5° C. The operator pierces a seal of the bottle 110a with the spike of the bottle connector 130a. Then he turns the bottle 110a (with the bottle connector 130a connected thereto) up-side-down, he inserts the bottle connector 130a into the connection port 132a (so as to connect its connection element to the connection element 143a), he mounts the protective cover 120a on the bottle holder 115a (so as to protect and thermally insulate the bottle 110a) and then he fills the drip chamber 142a with the contrast agent (by repeatedly manually squeezing the reservoir 142a). At this point, the operator programs the control unit 155 (either at the control unit 155 or at the injector remote console) by entering specific information relating to the contrast agent of the bottle 110a (for example, its brand name and volume). The operator repeats the same operations, if necessary, to install the other bottle 110b (which may contain the same contrast agent of bottle 110a or a different contrast agent or a saline solution). The control unit 155 then displays a message on its screen prompting the operator to install the patient set 145.

According to the present disclosure, the operator can easily and quickly prepare the patient set 145 by positioning the delivery tube 146 into the second loading component (i.e. the loader) 230 of the peristaltic pump 200, this operation being performed separately from the injection system 100. As better shown in FIG. 8, the peristaltic pump 200 is represented in its opened loading configuration according to which the second loading component 230 is axially retracted in a distal direction (see arrow A) till the small bumps 221 of the tabs 220 of the first housing component 210 get into contact with the ridges (e.g. 248) of the grooves (e.g. 247) of the second loading component 230, and the ramp support 249 of the second loading component 230 faces the proximal end of the curved depressed portion 224 of the first housing component 210, thereby becoming part of the guiding path 240. In this opened loading configuration the operator places and blocks the connection element 147 of the delivery tube 146 within the supporting element 213 of the first housing component 210 and then he fits the delivery tube 146 along the guiding element 215. Therefore the delivery tube 146 results in being positioned radially external to the rollers 235 arrangement of the second loading component 230, within the curved depressed portion 224 of the first housing component 210 and then along the third path 240c, thereby reaching the exit port 244 at the distal end surface 231 of the second loading component 230.

Figure 8:
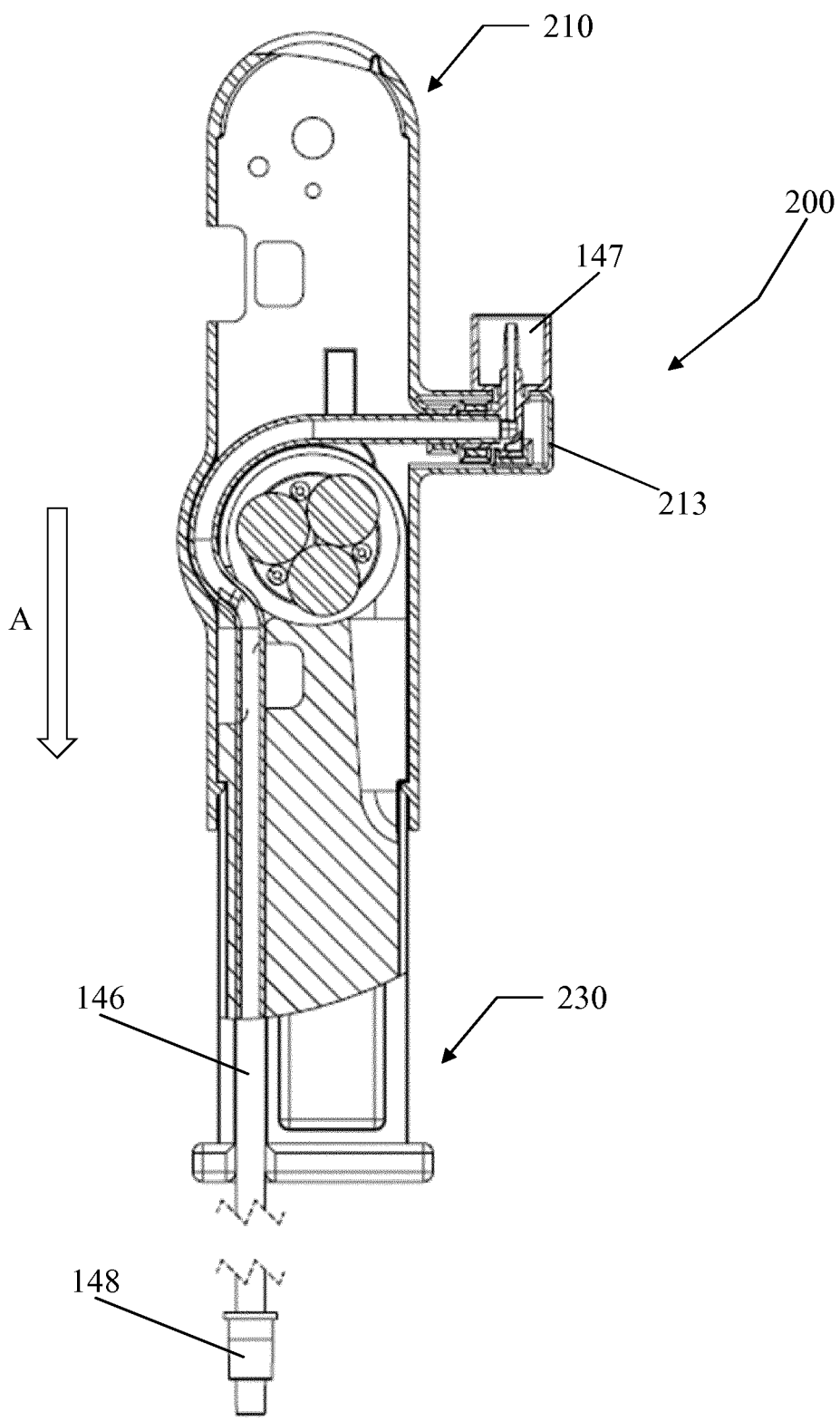
FIG. 8 shows a partial longitudinal cross-section of the peristaltic pump in its opened, non-operative condition.
Figure 9:
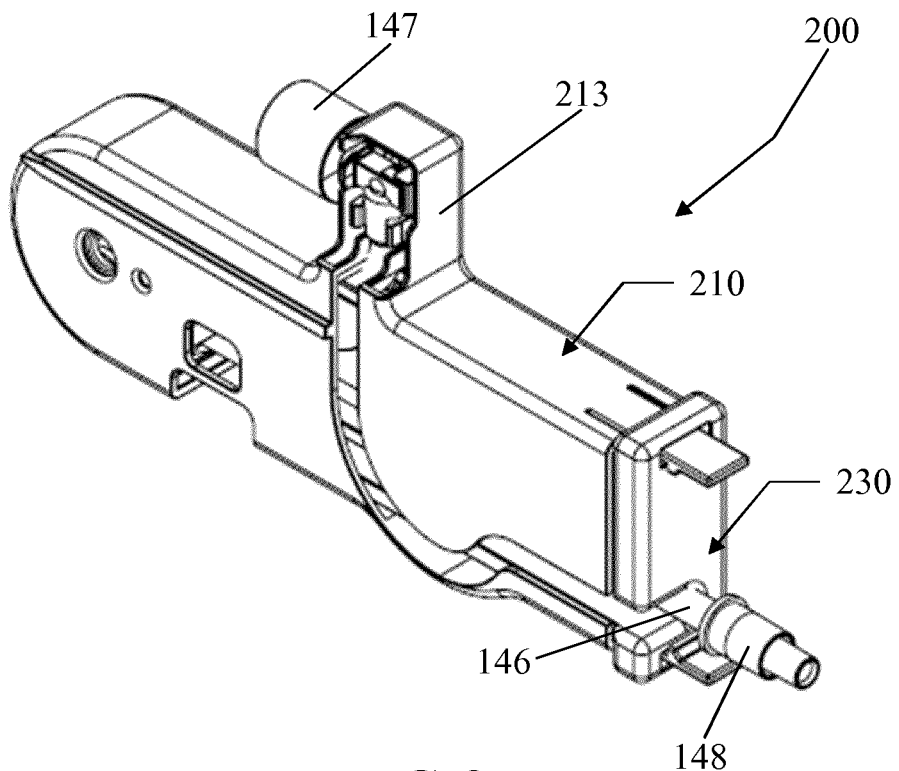
FIG. 9 and FIG. 10 show a perspective and a partial longitudinal cross-section, respectively, of the peristaltic pump in its operative condition, ready for being inserted into the pressurizing unit of an injection system.
Figure 10:
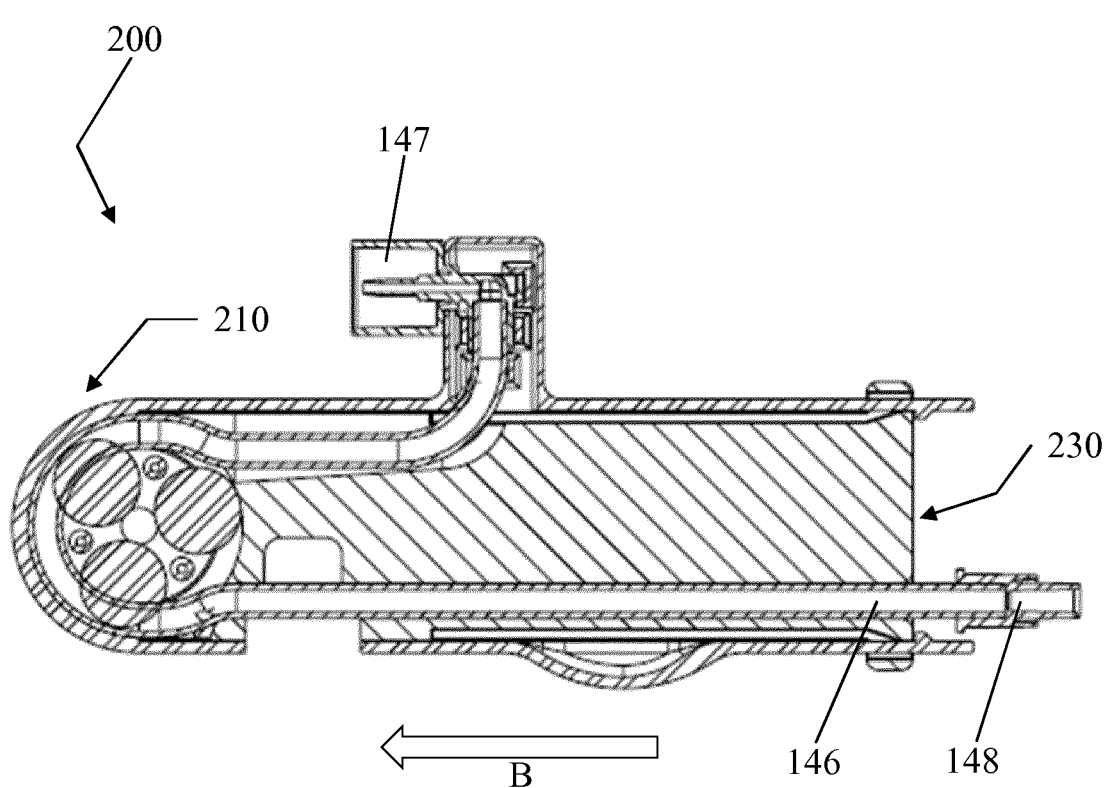

As soon as the delivery tube 146 is properly loaded within the peristaltic pump 200 as shown in FIG. 8, the operator advances the second loading component 230 by pushing it in a proximal direction (see arrow B in FIG. 10), thereby achieving a closed, operative configuration according to which the first 210 and the second 230 components are fully axially engaged, as better represented in FIG. 9.

Thereafter the operator can introduce the peristaltic pump 200 into the dedicated slot of the pressurizing unit 140, connect the peristaltic pump 200 to the T-connector 144 and arm the injector which will be ready to run a predetermined selected injection procedure.

In case the patient set 145 is for multiple use (as shown in FIG. 2), the operator further connects the connection element 150 of the additional patient line 151 to the connection element 148 of the delivery tube 146.

Successively the operator separately primes each transfer line 141a, 141b and 141c by selecting a corresponding priming function on the control unit 155 (or at the remote console), so as to eliminate air bubbles that are possibly present within the transfer lines 141a, 141b and 141c, the delivery line 146 and/or the (possible) additional patient line 151. Alternatively and preferably, the priming phase is advantageously automatically performed by the injection system without the need for the operator to execute it manually. Once this priming phase has been terminated (and no air is sensed in the injection system 100), the operator finally connects the connection element 148 of the patient set 145 (in case the patient set is for a single use) or the connection element 152 of the additional patient line 151 (in case the patient set is for multiple use) to the connection element of a peripheral catheter (not shown in the figures) which has already been inserted into the patient's vasculature.

Then the operator programs the control unit 155 (or the remote console) by entering or selecting information related to the injection examination to be performed (for example, the needle gauge of the peripheral catheter, the injection protocol comprising one or more injection phases, each injection phase being defined by the type, volume and flow rate of the medical fluids to be injected, possibly selected among pre-defined injection protocols for different types of injection procedures and correlated scan examinations).

The injection protocol (i.e. the number of injection phases, the sequence of injection phases, the injection parameters like flow rate and duration time, contrast agent and saline details, needle gauge) specific for a given patient to be examined can be manually introduced by the operator through the control unit 155 (or the remote console). Alternatively, the operator can download a desired injection protocol from a removable memory, such as a USB flash drive. Alternatively, the operator can download a desired injection protocol, as well as the relevant data of the patient to be examined, from a server which can connect more than one injection system 100 and, in case, also a plurality of clinical premises.

Finally the operator can start the scan examination which combines the functionalities of the injection system with the functionalities of the imaging device, the latter being operated in conjunction with the injection system that provides for the contrast agent activity which is used during the scan procedure. At the end of the scan examination, the injection system 100 stops automatically and the operator disconnects the patient set 145 or the additional patient line 151 from the peripheral catheter.

As mentioned above, if the patient set 145 is of the single-use type, the operator disengages the peristaltic pump 200 from the pressurizing unit 140, he opens the peristaltic pump by unblocking the small bumps 221 from the corresponding slots 245, 246 thereby allowing the axial sliding retraction of the second loading component 230 from the first housing component 210, and he finally removes and discards the used delivery tube 146. On the contrary, if the patient set 145 is of the multiple-use type and its usage time (typically 12 hrs) has not elapsed yet, the operator keeps the peristaltic pump 200—and the delivery tube 146 loaded therein—within the pressurizing unit 140 and he finally removes and discards only the used additional patient line 151. At this point the injection procedure of the examined patient can be considered completed.

As mentioned above, if the delivery arrangement 135 is a disposable element that is required to be changed every 24 hours, at the end of the injection procedure the delivery arrangement 135 is not discarded if its usage time has not elapsed yet, and it remains installed on the injector, ready for a new patient to be injected and a new injection procedure to be started.

The injection system 100 of FIG. 1 and FIG. 2 comprises three separate supply stations 105a, 105, 105c. However, the present disclosure can be applied to an injection system that is provided with a single supply station (not shown). Analogously, the present disclosure can be applied to an injection system that is provided with two separate supply stations (not shown).

According to a further embodiment (not shown) of the present disclosure, the peristaltic pump is at least partially integral with the pressurizing unit of the injection system and it is not removable from the pressurizing unit. Therefore, the operator is not requested to manipulate the peristaltic pump and manually installing/uninstalling it into/from the injector head and thus the operation of loading the delivery tube is not performed separately from the injection system 100. According to this embodiment the operator is only requested to unblock the second loading component from the first housing component by axially retracting the second loading component with a sliding movement towards a distal direction (i.e. towards the operator) as previously disclosed. In this way the guiding path is rendered accessible to the operator and he can properly load the delivery tube and then advance in the proximal direction the second loading component with respect to the fixed first housing component in order to achieve a closed, operative configuration.

According to an alternative embodiment (not shown), the sliding motion of the second loading component with respect to the fixed first housing component in order to open and close the peristaltic pump is automatically performed by the injection system, e.g. by providing a dedicated motor. In this case, the operator is requested only to suitably load the delivery tube within the guiding element and he does not even need to touch the peristaltic pump, fact which even more remarkably reduces the risk of possible contaminations.

The automatic opening and closing of the peristaltic pump (i.e. the automatic sliding motion of the second loading component with respect to the fixed first component) can be actuated by the operator (e.g. by pressing a button on the injector control unit or remote control) or it can be done automatically by the injection system that recognizes the steps sequence of an injection procedure and it senses if a delivery tube is properly installed and when a used delivery tube has to be discarded and substituted with a new one.

Modifications

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

In an embodiment, the injection system is for injecting one or more fluids into a patient. However, the fluids may be in any number and of any type (for example, whatever medical fluid to be used in a generic medical application for diagnostic or therapeutic purposes, such as a drug or a body fluid, or more generally to be used in any other treatment, such as for cosmetic purposes); moreover, the fluid may be injected in any way (for example, intra-arterially) into any (human or animal) patient.

In an embodiment, the injection system comprises one or more supply stations each one for supplying one of the fluids to be injected. However, the injection system may comprise any number of supply stations (down to a single one) for supplying the same or different fluids (in any combination).

In an embodiment, the injection system is for injecting the fluids into the patient during a scan examination thereof; the fluids are one or more medical fluids comprising a contrast agent and/or a saline solution. However, the injection system may be used for any scan examination (for example, in MR, nuclear or ultrasound imaging applications); moreover, the injection system may be used with any contrast agent (for example, a barium-based contrast agent such as barium sulfate, gadolinium, a radioisotope, a suspension of gas-filled microbubbles), any saline solution (for example, with the addition of dextrose), any combination thereof or more generally with any medical fluid(s).

The invention claimed is:

1. A peristaltic pump (200) comprising a first housing component (210) and a second loading component (230),
   wherein the second loading component (230) has a first (proximal) end region (232) and a second (distal) end region (234),
   wherein the first housing component (210) defines an external casing of the peristaltic pump (200) and has a longitudinal axis with a proximal end (212) and a distal end (211), such that the second loading component (230) is capable of being snapped into the first housing component (210) by moving the second loading component (230) along the longitudinal axis in a proximal direction (B) towards the proximal end (212) of the first housing component (210) and is capable of being retracted from the first housing component (210) by moving the second loading component (230) along the longitudinal axis in a distal direction (A) towards the distal end (211) of the first housing component (210),
   said second loading component (230) being at least partially contained within said first housing component (210),
   and wherein said second loading component (230) comprises at least a couple of rollers (235) for engaging and squeezing a delivery tube (146) when, in operation, the second loading component (230) is fully snapped into said first housing component (210), the second loading component (230) further comprising a guiding path (240) for guiding the delivery tube (146) around said at least a couple of rollers towards an exit port (244) provided at a distal end surface (231) of the second (distal) end region (234) of the second loading component (230).

2. The peristaltic pump (200) according to claim 1, characterized in that the guiding path (240) of the second loading component (230) comprises a first path (240a) which is provided along a top portion of the second loading component and which extends from the first (proximal) end region (232) to a central region (233) of the second loading component.

3. The peristaltic pump (200) according to claim 1, characterized in that the guiding path (240) of the second loading component (230) comprises a second path (240b) which surrounds said at least a couple of rollers and which substantially extends around a circular profile of said first (proximal) end region (232).

4. The peristaltic pump (200) according to claim 1, characterized in that the guiding path (240) of the second loading component (230) comprises a third path (240c) which is provided along a bottom portion of the second loading component and which extends from the first (proximal) end region (232) to the second (distal) end region (234), said third path merging to the exit port (244) at the distal end surface (231) of the second loading component (230).

5. The peristaltic pump (200) according to claim 1, characterized in that the guiding path (240) of the second loading component (230) comprises a ramp support (249) for directing the delivery tube (146) towards said exit port (244).

6. The peristaltic pump (200) according to claim 1, characterized in that the first housing component (210) comprises a guiding element (215) for receiving the delivery tube (146), the guiding path (240) of the second loading component (230) cooperating with said guiding element (215) of the first housing component for positioning and guiding the delivery tube (146) within the peristaltic pump (200) towards said exit port (244) thereof.

7. The peristaltic pump (200) according to claim 2, characterized in that the first path (240a) merges with an exit port (243) provided on the top portion of the second loading component (230) so that, when the second loading component is fully snapped into the first housing component (210), said exit port (243) is located in correspondence of a supporting element (213) possessed by said first housing component, the delivery tube (146) being guided through said exit port (243) and fixed to said supporting element (213).

8. The peristaltic pump (200) according to claim 1, characterized in that the first housing component (210) comprises blocking means (219) for securing the first housing component (210) to the second loading component (230).

9. The peristaltic pump (200) according to claim 8, characterized in that the blocking means (219) comprises at least a tab (220) provided with a bump (221).

10. The peristaltic pump (200) according to claim 1, characterized in that the first housing component (210) has a substantially U-shape in longitudinal cross-section and it comprises a first (distal) end (211) that is opened for receiving the second loading component (230).

11. The peristaltic pump (200) according to claim 9, characterized in that the distal end surface (231) of the second loading component (230) comprises at least one slot (245; 246) for receiving a corresponding tab (220) of the blocking means (219) of the first housing component (210).

12. A patient set (145) comprising:
a peristaltic pump (200) according to claim 1, and
a delivery tube (146) received by the first housing component (210) and the second loading component (230) of said peristaltic pump.

13. An injection system (100) comprising:
at least one supply station (105a; 105b; 105c) for supplying a medical fluid to be injected into a patient's vasculature;
a pressurizing unit (140) comprising a motor for pressurizing the medical fluid received from said at least one supply station;
a delivery arrangement (135) in fluid communication with said at least one supply station, and
a patient set (145) in fluid communication with said delivery arrangement for delivering the pressurized medical fluid to the patient, said patient set comprising a peristaltic pump (200) according to claim 1.

14. The injection system (100) according to claim 13, characterized in that, in operation, the peristaltic pump (200) is coupled with said pressurizing unit and a delivery tube (146) is engaged by said peristaltic pump for delivering the pressurized medical fluid to the patient.

15. The injection system (100) according to claim 13, characterized in that the peristaltic pump (200) is detachably coupled with the pressurizing unit (140).

16. The injection system (100) according to claim 13, characterized in that the peristaltic pump (200) is integral with the pressurizing unit (140).

17. The injection system (100) according to claim 16, characterized in that the first housing component (210) is fixed to the pressurizing unit (140) and the second loading component (230) is slidably movable with respect to said first housing component (210) and inside thereto.

18. The injection system (100) according to claim 17, characterized in that the sliding motion of the second loading component (230) with respect to the first housing component (210) is performed automatically by the injection system (100).

19. A method of operating an injection system (100), the injection system comprising: a pressurizing unit (140), at least one supply station (105a; 105b; 105c) for supplying a fluid to the pressurizing unit and a peristaltic pump (200) coupled with said pressurizing unit, said peristaltic pump comprising a first housing component (210) and a second loading component (230), wherein the second loading component (230) has a first (proximal) end region (232) and a second (distal) end region (234), wherein the first housing component (210) defines an external casing of the peristaltic pump (200) and has a longitudinal axis with a proximal end (212) and a distal end (211), said second loading component comprising at least a couple of rollers (235) and a guiding path (240), said method comprising the steps of:
axially retracting along the longitudinal axis in a distal direction (A) the second loading component (230) towards the distal end (211) of the first housing component (210), so that the peristaltic pump (200) reaches an opened loading configuration;
positioning a delivery tube (146) about said at least a couple of rollers and along said guiding path (240) towards an exit port (244) provided at a distal end surface (231) of the second (distal) end region (234) of the second loading component;
snapping said second loading component (230) into said first housing component (210) so that the peristaltic pump (200) reaches a closed operative configuration, and
operating the pressurizing unit (140) to rotate the at least a couple of rollers (235) for engaging and squeezing the delivery tube.

20. The method of operating the injection system (100) according to claim 19, wherein the step of snapping comprises the step of axially sliding the second loading component (230) along the longitudinal axis in a proximal direction (B) towards the proximal end (212) of the first housing component (210) inside thereto.

21. The method of operating the injection system (100) according to claim 19, wherein the method further comprises the step of introducing the peristaltic pump (200) into a slot of the pressurizing unit (140).

22. The method of operating the injection system (100) according to claim 19, wherein the method further comprises the step of unblocking the second loading component (230) from the first housing component (210), said step of unblocking being performed before said step of retracting.

23. The method of operating the injection system (100) according to claim 19, wherein the method further comprises the step of blocking the second loading component (230) to the first housing component (210), said step of blocking being performed after said step of snapping.

24. The method of operating the injection system (100) according to claim 19, wherein the retracting step and/or the snapping step is automatically performed by the injection system (100).

\* \* \* \* \*